(12) United States Patent
Smith et al.

(10) Patent No.: US 11,497,414 B1
(45) Date of Patent: Nov. 15, 2022

(54) BREATH ANALYSIS DEVICE WITH REGULATED FLOW DURING EXHALATION

(71) Applicant: Invoy Holdings, Inc., Irvine, CA (US)

(72) Inventors: Zachary B. Smith, Phoenix, AZ (US); Connie Kim, Garden Grove, CA (US); Lubna M. Ahmad, Chandler, AZ (US); Ronald J. Schoenbaum, Newport Coast, CA (US)

(73) Assignee: Invoy Holdings, Inc., Irvine, CA (US)

( * ) Notice: Subject to any disclaimer, the term of this patent is extended or adjusted under 35 U.S.C. 154(b) by 363 days.

(21) Appl. No.: 16/837,780

(22) Filed: Apr. 1, 2020

Related U.S. Application Data

(60) Provisional application No. 62/847,106, filed on May 13, 2019.

(51) Int. Cl.
*A61B 5/08* (2006.01)
*G01N 33/497* (2006.01)
*A61B 5/097* (2006.01)

(52) U.S. Cl.
CPC .............. *A61B 5/082* (2013.01); *A61B 5/097* (2013.01); *G01N 33/497* (2013.01); *G01N 2033/4975* (2013.01)

(58) Field of Classification Search
CPC ...... A61B 5/082; A61B 5/097; G01N 33/497; G01N 2033/4975; G01N 33/64; A61M 2016/0027; A61M 16/024
See application file for complete search history.

(56) References Cited

U.S. PATENT DOCUMENTS

| | | | |
|---|---|---|---|
| 5,174,959 A | 12/1992 | Kundu et al. | |
| 9,486,169 B1* | 11/2016 | Ahmad | A61B 5/150412 |
| 9,643,186 B1* | 5/2017 | Ahmad | B01L 3/52 |
| 9,709,581 B1* | 7/2017 | Gordon | C07D 311/82 |
| 10,226,201 B2 | 3/2019 | Ahmad et al. | |
| 10,682,072 B2 | 6/2020 | Ratto et al. | |
| 2005/0177056 A1 | 8/2005 | Giron et al. | |
| 2005/0177057 A1 | 8/2005 | Friedman et al. | |
| 2008/0004542 A1 | 1/2008 | Allen et al. | |
| 2013/0303929 A1 | 11/2013 | Martino et al. | |
| 2014/0276100 A1* | 9/2014 | Satterfield | A61B 5/7271 |
| | | | 600/476 |
| 2015/0335267 A1 | 11/2015 | Cormier et al. | |
| 2016/0146779 A1 | 5/2016 | Gallagher et al. | |

(Continued)

*Primary Examiner* — Orlando Bousono
(74) *Attorney, Agent, or Firm* — Knobbe, Martens, Olson & Bear, LLP

(57) ABSTRACT

A pump-less breath analysis device regulates the flow of breath past a nanoparticle sensor (or other semiconductor sensor) by dynamically adjusting the state or position of a valve as the user exhales into the device. The valve controls the flow of incoming breath between two flow paths: a venting path through which breath exits the device without passing by the nanoparticle sensor, and a sensing path that includes the nanoparticle sensor. In some embodiments, the valve is controlled by a processor that monitors pressure produced by the user's exhalation force. Based on these real-time pressure measurements, the processor adjusts the valve to maintain the pressure, and thus the flow rate, in the sensing path within a desired range. The processor may also use the pressure measurements to determine whether the characteristics of the user's exhalation are sufficient to generate a valid measurement.

15 Claims, 2 Drawing Sheets

(56) References Cited

U.S. PATENT DOCUMENTS

| | | | |
|---|---|---|---|
| 2016/0150995 A1 | 6/2016 | Ratto et al. | |
| 2016/0242674 A1* | 8/2016 | Ahmad | A61B 5/082 |
| 2016/0331272 A1* | 11/2016 | Ahmad | A61B 5/082 |
| 2016/0370377 A1* | 12/2016 | Ahmad | A61B 5/150412 |
| 2017/0119279 A1* | 5/2017 | Ahmad | A61B 5/082 |
| 2017/0119280 A1* | 5/2017 | Ahmad | A61B 5/097 |
| 2017/0224251 A1* | 8/2017 | Ahmad | A61B 5/087 |
| 2018/0056302 A1* | 3/2018 | Ahmad | G01N 33/542 |
| 2019/0120821 A1* | 4/2019 | Atsalakis | A61B 5/0803 |

* cited by examiner

BREATH ANALYSIS DEVICE WITH REGULATED FLOW DURING EXHALATION

PRIORITY CLAIM

This application claims the benefit of U.S. Provisional Appl. No. 62/847,106, filed May 13, 2019, the disclosure of which is hereby incorporated by reference.

BACKGROUND OF THE INVENTION

Technical Field

The present invention relates to breath analysis devices for measuring ketones or other analytes in breath.

Description of the Related Art

Various types of breath analysis devices exist for allowing individuals to measure their breath ketone levels, such as acetone levels. These devices are sometimes provided to participants in health programs, such as Keto diet programs, to enable the participants to monitor fat metabolism.

Many commercially-available breath analysis devices use a nanoparticle sensor, or another type of semiconductor sensor, to measure ketone or other analyte levels. Although these devices are typically small and convenient to use, they typically do not generate accurate ketone measurements. As a result, they typically are not useful for non-Keto diet applications in which it is desirable to measure ketone levels falling below about 9 parts per million (PPM).

SUMMARY

One known method for improving measurement accuracy in these types of devices is to include within the device a pump that controls the flow rate of the breath sample past the nanoparticle sensor. The use of a pump, however, adds to the cost and complexity of the device, and typically requires the device to include or attach to a breath capture chamber that captures the breath sample before it is pumped. Further, the task of capturing the breath sample before it is analyzed introduces delay into the ketone measurement process.

The present disclosure addresses these deficiencies by providing a pump-less breath analysis device that regulates the flow of breath past the nanoparticle sensor (or other semiconductor sensor) by dynamically adjusting the state or position of a valve as the user exhales into the device. The valve controls the flow of incoming breath between two flow paths: a venting path through which breath exits the device without passing by the nanoparticle sensor, and a sensing path that includes the nanoparticle sensor. In some embodiments, the valve is controlled by a processor that monitors pressure produced by the user's exhalation force. Based on these real-time pressure measurements, the processor adjusts the valve so as to maintain the pressure, and thus the flow rate, in the sensing path within a desired range. The processor may also use the pressure measurements to determine whether the characteristics of the user's exhalation are sufficient to generate a valid measurement.

DETAILED DESCRIPTION OF THE PREFERRED EMBODIMENTS

Figure 1:
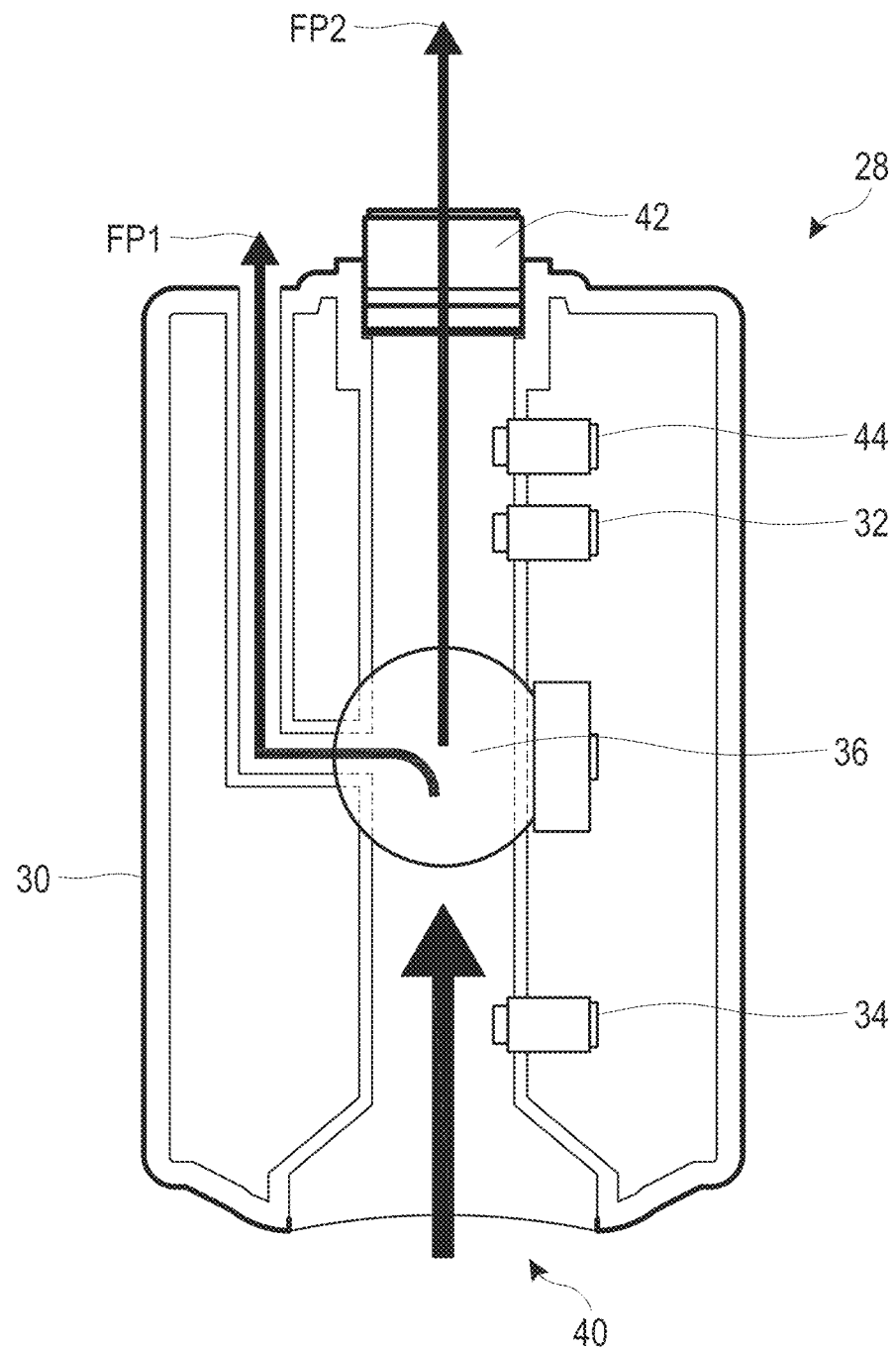
FIG. 1 illustrates a breath analysis device according to one embodiment.

FIG. 1 illustrates a handheld, pump-less, breath analysis device 28 according to one embodiment. The device includes a housing 30 that houses a nanoparticle-based ketone sensor 32, a pressure sensor 34, a processor-controlled valve 36, internal tubes or conduits for the flow of breath along the flow paths shown by the arrows, and a processor and associated electronics (not shown). The breath analysis device 28 also includes a breath input port 40 into which a user can blow or exhale a breath sample. The nanoparticle sensor 32 is preferably designed to measure breath acetone levels. The device is preferably sized to fit in the hand of the user during use.

Breath exhaled into the breath input port 40 exits the device along flow path 1 (FP1) and flow path 2 (FP2), with the fraction exiting along FP1 versus FP2 depending upon the degree to which the valve 36 is open. Because the breath flows along these paths FP1 and FL2 as the direct result of the exhalation force created by the user, no pump or other pressure-creating device is needed. The processor-controlled valve 36 preferably includes or is coupled to a stepper motor capable of adjusting the valve between a plurality of partially-open positions. The number of such positions is preferably at least 8, and can be significantly higher. An optional one-way valve 42 at the effluent end of flow path 2 prevents air from flowing back into the device. As shown in FIG. 1, a second pressure sensor 44 may optionally be positioned along flow path 2. Breath that flows along flow path 2 passes by the nanoparticle sensor 32 and is used to generate a ketone measurement. Flow path 2 is thus a "sensing path," and flow path 1 a "venting path." As explained below, the venting path, FP1, may be omitted in some embodiments.

The device 28 may also include a wireless transceiver, such as a Bluetooth or Bluetooth Low Energy (BLE) transceiver, that enables the device 28 to communicate wirelessly with a mobile application running on a phone, tablet, or other communication device of the user. In addition, the device 28 may include an LED, a sound generator, a haptic signal generator, a display, and/or another type of signal generator for conveying device status information to the user (as explained below). The device 28 may also include any of the structures and features disclosed in U.S. patent application Ser. No. 15/156,188, filed May 16, 2016, the disclosure of which is hereby incorporated by reference.

To obtain an accurate ketone measurement, the rate at which breath flows along the sensing path FP2 (and thus past or along the nanoparticle sensor 32) should be tightly regulated. In the illustrated embodiment, the task of regulating this flow rate is controlled by the processor-controlled valve 36 based on real-time pressure measurements generated by one or both of the pressure sensors 34, 44. More specifically, based on the real-time pressure measurements, the processor controls the state of the valve 36 (and specifically the degree to which it is open) during exhalation to maintain the pressure in the region of the nanoparticle sensor 32 within a selected range, such as 14.45-15.10 pounds per square inch (psi), 14.45-14.70 psi, 14.45-14.80 psi, 14.45-14.90 psi, 14.60-14.80 psi, 14.65-14.90 psi, 14.65-15.0 psi, 14.75-15.10 psi 14.45-14.60 psi, 14.45-14.70 psi, 14.45-14.80 psi, 14.45-14.90 psi, 14.60-14.80 psi, 14.65-14.90 psi, 14.65-15.0 psi, or 14.75-15.10 psi. By maintaining the pressure within this range, the valve also maintains the flow rate past the nanoparticle sensor within a desired range, such as 3.50-5.50 liters per minute (LPM), 5-8 LPM, 5-10 LPM, 10-12 LPM, 10.25-12.50 LPM, or 12-25 LPM.

Thus, for example, if the user blows harder than average in one embodiment, the processor partially closes the valve relative to its middle or average state (e.g., from 50% open state to 35% open) to compensate for the higher-than-average pressure in the chamber upstream from the valve 36. If the user exhales with less than an average force, the processor partially opens the valve relative to its average state (e.g., from 50% open to 65% open) to compensate for the lower-than average pressure upstream from the valve 36. And if the user exhales with a force that varies over time, the processor varies the valve position substantially in real time to compensate for the pressure variations upstream from the valve 36.

During exhalation, the pressure downstream from the valve 36 will ordinarily be lower than the pressure upstream from the valve by predictable amount that depends on the state of the valve; this relationship between upstream pressure, downstream pressure and valve state can be recorded in a look-up table stored in a memory of the device 28, and can be used to dynamically control the valve.

Thus, in some embodiments, the processor may control the valve 36 based on a look-up table (or alternatively an equation) that maps pressure readings sensed by the upstream pressure sensor 34 to valve positions. The downstream pressure sensor 44, if provided, may alternatively be used as the source of pressure readings used to control the valve 36, or may be used as a secondary source of real-time pressure data for controlling the valve. In some embodiments in which a downstream pressure sensor 44 is provided, real-time pressure measured by this sensor may be used to implement a feedback loop that seeks to minimize the difference between the actual downstream pressure and the target downstream pressure. In some embodiments in which both an upstream and a downstream pressure sensor are provided, the processor controls the state of the valve 36, and thus regulates flow, based on the differential pressure between the upstream pressure sensor 34 and the downstream pressure sensor 44. For example, a look-up table or equation that maps differential pressure to valve position may be used, or a feedback look may be used that seeks to maintain the differential pressure approximately constant during exhalation.

Figure 2:
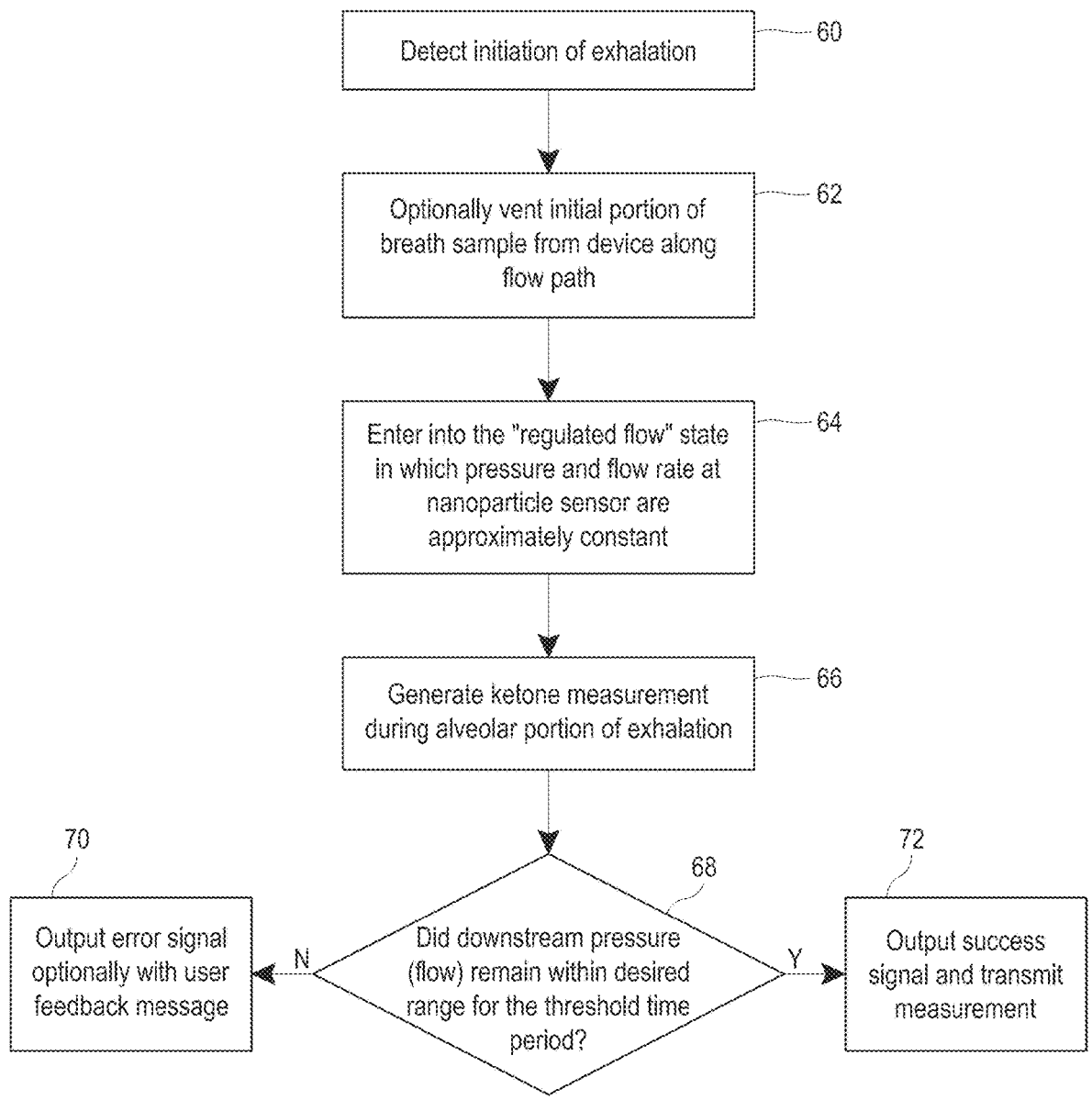
FIG. 2 illustrates a process implemented by the processor of the breath analysis device during a breath test.

FIG. 2 illustrates one example of a process that may be implemented by the breath analysis device 28 when a user exhales a breath sample. This process may be implemented by the processor under the control of program code (e.g., firmware instructions) stored in a memory of the device. The processor may, when the device 28 is turned on, perform a warm-up cycle (not shown) to prepare the nanoparticle sensor 32 for use. Upon completion of the warm-up cycle, the device 28 may output a signal (such as by illuminating an LED or outputting a sound) to inform the user that it is ready to accept a breath sample. At this point the process enters into a loop in which it monitors the upstream pressure to determine whether the user is exhaling into the device. If the pressure increases by selected threshold (e.g., over a selected time interval such as 0.5 seconds, 1 second, 2 seconds, etc.), the process treats the pressure increase as the initiation of an exhalation event (block 60).

As illustrated by block 62, the process then optionally vents an initial portion of the exhaled breath sample from the device 28 by placing or maintaining the valve 36 in a position in which all or substantially all incoming breath is routed out along the venting path, (FP1 in FIG. 1). The valve 36 may be maintained in this position long enough to vent the "dead space" air in the user's trachea and lungs from the device, so that the breath that is subsequently routed along the sensing path (FP2) consists essentially or entirely of deep alveolar breath. The venting time may be a fixed value in the range of about 2 to 4 seconds, or may be a variable value that is dependent upon the pressure level sensed by the upstream pressure sensor 34, the user's average exhalation duration as measured by the device, and/or other factors. Although such venting of the initial breath sample portion can improve the accuracy of ketone measurements, it is not required.

In block 64, the process enters into a "regulated flow" state in which the valve 36 is dynamically controlled so as to maintain the pressure downstream from the valve within a target range, such as one of the pressure ranges listed above, during exhalation of alveolar breath. As explained above, the purpose of this step is to maintain the alveolar breath flow rate past the nanoparticle sensor 32 at a desired, and approximately constant level (or within an acceptable range) for a sufficient time period (e.g., 1 to 5 seconds) for the nanoparticle sensor to generate an accurate ketone measurement (block 66). This is accomplished by dynamically varying the size of the valve's opening through which breath must flow to reach the nanoparticle sensor. As mentioned above, the flow may be regulated based on real-time readings from an upstream pressure sensor 34, from a downstream pressure sensor 44, or from both an upstream and a downstream pressure sensor (e.g., based on the real-time difference between the upstream and downstream pressure).

In decision block 68, which may be performed either during or after the task of generating the ketone measurement, the process determines whether the exhalation characteristics during the regulated flow phase satisfy the criteria for generating a valid ketone measurement. Preferably, this involves determining whether the pressure downstream from the valve 36 remains (or remained) within a target range for a selected time interval, such as 3 seconds, 4 seconds, or some other duration. For example, the process may generate the ketone measurement 7 seconds after exhalation begins, and may treat this measurement as invalid if the downstream pressure did not remain in the target range for the 3-second time period starting at 4 seconds from initiation of exhalation. In embodiments in which the device 28 includes a downstream pressure sensor 44, this task 68 is preferably performed based partly or wholly on the pressure monitored by that sensor 44. If no downstream pressure sensor 44 is provided, the pressure monitored by the upstream pressure sensor 34 may be used. A ketone measurement may be treated as invalid in block 68 if, for example, the user did not blow hard enough, did not blow long enough, or did not blow with a sufficiently constant force.

As indicated by block 70 in FIG. 2, if the exhalation did not satisfy the criteria for generating a valid ketone measurement, the device 28 outputs an error signal. For example, the device may change the color of an LED to red, may output an error tone, and/or may transmit an error message to the user's mobile phone for display by a mobile application. As indicated by block 72, if the exhalation characteristics were satisfactory, the device 28 outputs a success signal and transmits the ketone measurement to the mobile device for display by the mobile application.

In some embodiments, the processor of the breath analysis device 28 (or possibly the processor of a separate device) may execute a compensation algorithm that adjusts the ketone measurement to compensate for an imperfect or incomplete exhalation. For example, if the user's exhalation falls within the acceptable pressure range but is at the low end of that range (resulting in a lower than ideal pressure and flow rate at the nanoparticle sensor 32), the compensation algorithm may bump up, or otherwise adjust, the ketone measurement to account for the lower-than-ideal flow rate. Pressure data collected from the pressure sensor 34 may be used for this purpose. The amount of the adjustment may be determined by the processor using, e.g., a look-up table that maps average pressure values to ketone adjustment values. Such a look-up table may be generated using test data collected from actual or simulated exhalation tests in which gas with a known acetone concentration is passed through the device at various pressure levels and flow rates.

The accuracy of the ketone measurements can further be improved by reducing the quantity of moisture in the breath sample before it comes into contact with the nanoparticle sensor. Thus, although not shown in FIG. 1, the breath analysis device 28 may be configured to receive a disposable moisture-absorption element containing a desiccant. For example, the housing 30 may be configured to receive an insertable desiccant cartridge that, when inserted, becomes part of the sensing flow path (FP2) upstream from the nanoparticle sensor 32. The cartridge may be a single-use cartridge, or may contain enough desiccant for multiple breath tests. As a further enhancement, a moisture sensor (not shown) may be provided along the sensing flow path and used to determine whether the moisture content is too high (e.g., exceeds a selected threshold) for generating a valid ketone measurement. If the moisture level is too high, the device 28 may output a corresponding error signal indicating to the user that the desiccant cartridge needs to be replaced.

The likelihood of the user completing an exhalation of sufficient duration can be increased significantly by notifying the user of how much longer they need to exhale. Thus, in some embodiments, during the exhalation process, the breath analysis device 28 and/or the mobile application outputs an indication how much longer the user needs to exhale. This indication may, for example, be a visual, audible, or haptic signal that is output by the breath analysis device 28 when a selected amount of time, such as one second or two seconds, remains before exhalation is complete. For instance, an LED that is visible during exhalation may be illuminated in a particular color or strobed at this point in time. As another example, the mobile application may display a numerical countdown timer, or may display a graphical indication of the amount of time remaining. In embodiments in which the user is required to exhale a threshold volume of breath, the breath analysis device's processor may determine or estimate the amount of time remaining based on the output of the pressure sensor 34 or a flow sensor. In embodiments in which the user is required to exhale for a fixed amount of time, the processor may determine the amount of time remaining based solely on a timer that is started when the user begins to exhale.

In other embodiments of the device 28, the venting path FP1 may be eliminated, or may be included but only used to vent an initial portion of the breath sample from the device. In these embodiments, when the user is blowing too hard, the processor, by adjusting the state of the valve, narrows the opening through which breath must flow to reach the nanoparticle sensor, causing the user to experience more flow resistance and reducing the rate of flow. And when the user is not blowing hard enough, the processor adjusts the valve in the opposite direction to expand the opening and reduce the flow resistance experienced by the user, enabling the user to exhale at a greater flow rate.

In embodiments in which the venting path is eliminated, the valve 36 may optionally be positioned downstream from the nanoparticle sensor 32. In addition, because the initial portion of the breath sample flows past the nanoparticle sensor in these embodiments, the processor may effectively ignore the output of the nanoparticle sensor during this stage. For example, the output of the nanoparticle sensor may be ignored, or the nanoparticle sensor may be disabled, for the first N seconds of the exhalation, where N may, for example, be in the range of 2 to 5 seconds, and more preferably is in the range of 3 to 4 seconds.

Another variation is to use a flow rate sensor in place of the pressure sensor(s) 34, 44. For example a flow rate sensor may be positioned downstream from the valve 36 and used to measure the rate of flow past the nanoparticle sensor 32; the processor may in turn use the output of this flow rate sensor to adjust the valve so as to regulate the flow rate during exhalation.

Although the designs disclosed herein are particularly useful for measuring breath ketone levels (and particularly breath acetone levels), they may also be used to measure other breath analytes. Thus, the nanoparticle-based ketone sensor 32 in the disclosed designs may be replaced or supplemented with a nanoparticle-based or other sensor capable of measuring one or more other analytes.

What is claimed is:

1. A portable breath analysis device, comprising:
 a breath input port fluidly coupled to a flow path;
 a nanoparticle-based ketone sensor positioned along the flow path, the nanoparticle-based ketone sensor capable of measuring a ketone level in a breath sample that passes along the flow path under an exhalation force created by a user;
 a valve positioned along the flow path; and
 a processor configured to regulate a rate of flow of the breath sample past the nanoparticle-based ketone sensor by adjusting a state of the valve during exhalation of the breath sample by the user, the processor thereby configured to compensate for variations in an exhalation force created by the user.

2. The portable breath analysis device of claim 1, further comprising a pressure sensor positioned along the flow path, wherein the processor is configured to control the state of the valve based at least partly on pressure measurements generated by the pressure sensor.

3. The portable breath analysis device of claim 2, wherein the valve is positioned upstream from the nanoparticle-based ketone sensor, and the pressure sensor is positioned upstream from the valve.

4. The portable breath analysis device of claim 3, further comprising a second pressure sensor positioned downstream from the valve, wherein the processor is configured to adjust the state of the valve based additionally on an output of the second pressure sensor.

5. The portable breath analysis device of claim 4, wherein the processor is configured to adjust the state of the valve based at least partly on a differential pressure between the upstream pressure sensor and the downstream pressure sensor.

6. The portable breath analysis device of claim 1, further comprising a flow rate sensor positioned along the flow path, wherein the processor is configured to control the state of the valve based at least partly on flow rate measurements generated by the flow rate sensor.

7. The portable breath analysis device of claim 1, wherein the valve is coupled to a second flow path through which a portion of the breath sample is vented from the portable breath analysis device without passing by the nanoparticle-based ketone sensor.

8. The portable breath analysis device of claim 1, further comprising a stepper motor mechanically coupled to the valve, where in the processor adjusts the state of the valve by controlling the stepper motor.

9. The portable breath analysis device of claim 1, wherein the nanoparticle-based ketone sensor is a semiconductor sensor.

10. A process performed by a portable breath analysis device,
the portable breath analysis device comprising a breath input port fluidly coupled to a flow path, a nanoparticle-based ketone sensor positioned along the flow path and capable of measuring a ketone level in a breath sample that passes along the flow path under an exhalation force created by a user, and a valve positioned along the flow path, the process comprising, under control of a processor of the breath analysis device:
as the user exhales the breath sample into the breath input port, regulating a rate of flow of the breath sample along the flow path and past the nanoparticle-based ketone sensor by adjusting a state of the valve, the processor thereby configured to compensate for variations in an exhalation force created by the user; and
measuring the ketone level in the breath sample with the nanoparticle-based ketone sensor.

11. The process of claim 10, wherein the state of the valve is adjusted based at least partly on pressure measurements generated by a pressure sensor of the breath analysis device.

12. The process of claim 10, wherein the state of the valve is adjusted based at least partly on a differential pressure between an upstream pressure sensor positioned upstream from the valve and a downstream pressure sensor positioned downstream from the valve.

13. The process of claim 10, wherein the state of the valve is adjusted based at least partly on an output of a flow sensor that measures a flow rate along the flow path.

14. The process of claim 10, wherein the state of the valve is adjusted by controlling a stepper motor that is mechanically coupled to the valve.

15. The process of claim 10, wherein the nanoparticle-based ketone sensor is a semiconductor sensor.

* * * * *